DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED OCTOBER 3, 1972

903 O.G. 4

T903,003
CONTINUOUS HYDROGENATION PROCESS

Barry M. Mitchell, Rte. 12, Westbrook Drive,
Kingsport, Tenn. 37663

Filed Feb. 11, 1971, Ser. No. 114,730
Int. Cl. C07c *85/12*
U.S. Cl. 260—583 K
No Drawing. 8 Pages Specification

Both an improved process for the production of primary amines and a method of separating the hydrogenation catalyst from the reaction products are disclosed. By the process, an unsaturated nitrile and liquid ammonia are reacted in the presence of an excess of a polar solvent such as isopropanol to give a cyanoethylated product. The cyanoethylated product is then fed to a continuous hydrogenation process which utilizes a stirred reactor for the hydrogenation of the dinitriles. The hydrogenation catalyst employed in the process is formed from a material that is magnetically attracted by a magnet field and is separated from the hydrogenation reaction mixture by magnetic means.